(12) United States Patent
Griswold et al.

(10) Patent No.: US 8,401,643 B2
(45) Date of Patent: Mar. 19, 2013

(54) IMPLANTABLE MEDICAL SENSOR AND ANCHORING SYSTEM

(75) Inventors: Erik Griswold, Penngrove, CA (US); James Calvin Allan, Santa Rosa, CA (US); Rudy Beasley, Rohnert Park, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 62 days.

(21) Appl. No.: 13/109,426

(22) Filed: May 17, 2011

(65) Prior Publication Data

US 2012/0291788 A1  Nov. 22, 2012

(51) Int. Cl.
*A61B 19/00* (2006.01)

(52) U.S. Cl. ............ 607/23; 606/191; 606/200; 128/898

(58) Field of Classification Search ...................... 607/23
See application file for complete search history.

(56) References Cited

U.S. PATENT DOCUMENTS

| | | | |
|---|---|---|---|
| 5,147,370 A | 9/1992 | McManara | |
| 5,772,668 A | 6/1998 | Summers | |
| 5,967,986 A | 10/1999 | Cimochowski | |
| 6,331,163 B1 | 12/2001 | Kaplan | |
| 6,442,413 B1 | 8/2002 | Silver | |
| 6,451,025 B1 | 9/2002 | Jervis | |
| 6,468,301 B1 | 10/2002 | Amplatz | |
| 6,783,499 B2 | 8/2004 | Schwartz | |
| 6,855,155 B2 | 2/2005 | Denardo et al. | |
| 6,932,837 B2 | 8/2005 | Amplatz | |
| 7,481,771 B2 | 1/2009 | Fonseca | |
| 7,572,228 B2 | 8/2009 | Wolinsky | |
| 7,682,313 B2 | 3/2010 | Bodecker | |
| 7,769,420 B2 | 8/2010 | Silver | |
| 7,780,694 B2 | 8/2010 | Palmer | |
| 7,797,053 B2 | 9/2010 | Atkinson et al. | |
| 2002/0188207 A1 | 12/2002 | Richter | |
| 2004/0044393 A1 | 3/2004 | Yarden | |
| 2005/0187482 A1 | 8/2005 | O'Brien | |
| 2006/0009830 A1* | 1/2006 | Atkinson et al. | 607/126 |
| 2006/0122522 A1 | 6/2006 | Chavan | |
| 2006/0200031 A1* | 9/2006 | White et al. | 600/486 |
| 2006/0287700 A1 | 12/2006 | White | |
| 2007/0118039 A1* | 5/2007 | Bodecker et al. | 600/486 |
| 2007/0129637 A1 | 6/2007 | Wolinsky | |
| 2008/0021333 A1 | 1/2008 | Huelskamp | |
| 2008/0071178 A1* | 3/2008 | Greenland et al. | 600/486 |
| 2008/0071248 A1* | 3/2008 | Delgado et al. | 604/510 |
| 2009/0105557 A1 | 4/2009 | Najafi | |

FOREIGN PATENT DOCUMENTS

| | | |
|---|---|---|
| EP | 1068836 | 1/2002 |
| WO | WO99/34371 | 7/1999 |
| WO | WO02/054980 | 7/2002 |
| WO | WO2007/057739 | 5/2007 |
| WO | WO2008/144191 | 11/2008 |

* cited by examiner

*Primary Examiner* — Christopher D Koharski
*Assistant Examiner* — Michael Carey

(57) ABSTRACT

A medical device adapted to be implanted in a vessel of a human body includes a housing that contains a diagnostic or therapeutic module and an anchor for supporting the housing in an intended location and orientation within the vessel. The anchor is expandable from a low profile configuration adapted for delivery to an expanded configuration for engagement with the vessel wall. The anchor and a delivery catheter are adapted to enable the medical device to be retrieved and repositioned or removed from the vessel. The anchor is adapted to apply sufficient force against the vessel wall to maintain the anchor in place but less force than that required to provide scaffolding support for the vessel.

12 Claims, 8 Drawing Sheets

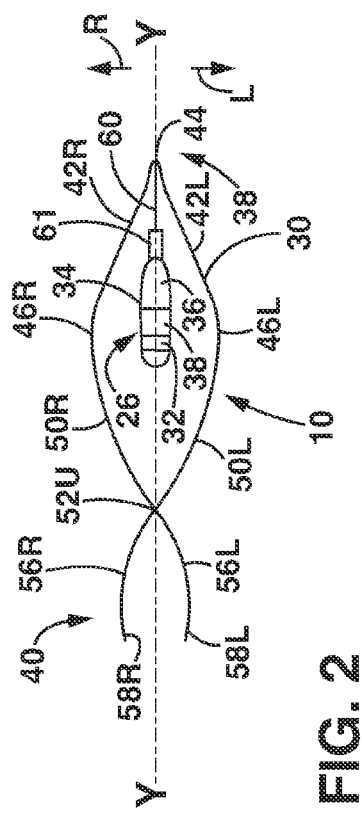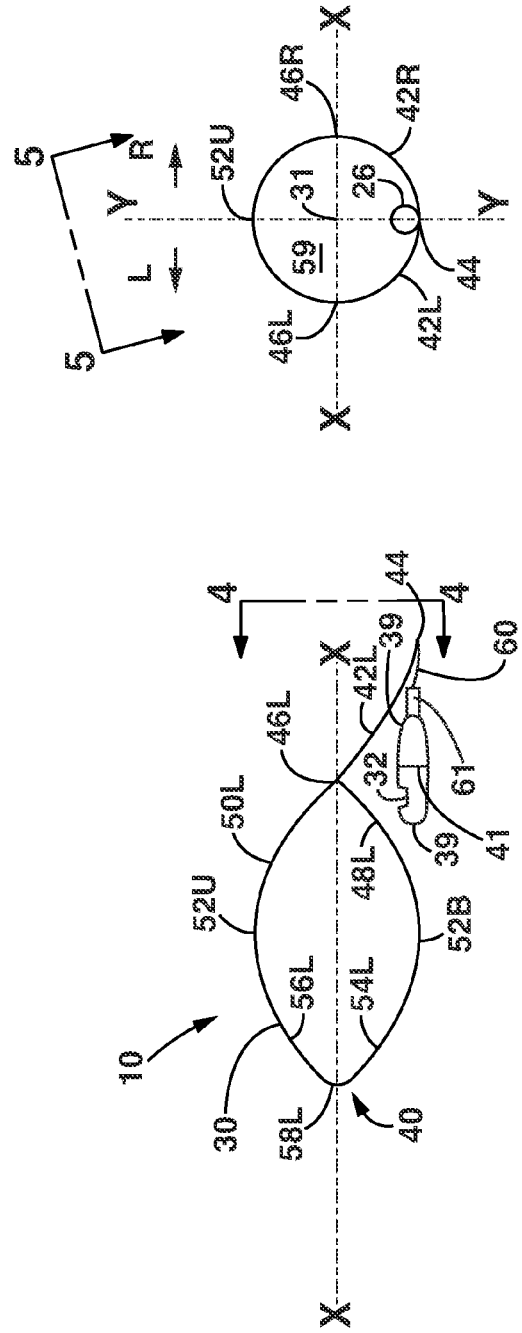

IMPLANTABLE MEDICAL SENSOR AND ANCHORING SYSTEM

FIELD OF THE INVENTION

The invention relates to implantable medical sensors and fixation or anchoring of such sensors in body lumens.

BACKGROUND

Various implantable medical devices have been clinically implanted or proposed for therapeutically treating or monitoring one or more physiological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, and pressure sensors, among others. Such devices may be associated with leads for electrical functions or may be wireless, with the ability to transmit data electronically either to another device implanted in the patient or to another device located externally of the patient, or both.

Although implantation of some devices requires a surgical procedure (e.g., pacemakers, defibrillators, etc.) other devices may be small enough to be delivered and placed at an intended deployment site in a relatively noninvasive manner, such as by a percutaneous delivery catheter. Depending on the nature, function and intended deployment site of the device, the manner in which the device is fixed in place and oriented in the body may affect the operation and accuracy of the device. Consequently, the means by which the device is fixed in place in the body can be a significant factor in its performance and utility.

By way of illustrative example, implantable miniature sensors have been proposed and used in blood vessels to measure directly the diastolic, systolic and mean blood pressures, as well as body temperature and cardiac output. Such direct in vivo measurement of hemodynamic parameters may provide significant information to clinicians to facilitate diagnostic and therapeutic decisions. If linked electronically to another implanted therapeutic device (e.g., a pacemaker), the data can be used to facilitate control of that device. Such sensors also, or alternatively, may be wirelessly linked to an external receiver. As one example, patients with chronic cardiovascular conditions, particularly patients suffering from chronic heart failure, may benefit from the use of implantable sensors adapted to monitor blood pressures. Promising indications have been reported for using such implantable sensors. Accurate knowledge of a patient's hemodynamic parameters can inform the decision whether to admit the patient to the hospital or whether the patient's condition can be managed with other therapies not requiring hospital admission. This is particularly so in connection with measurements of the blood pressure in the pulmonary artery that cannot be measured readily from an external location. Assessing a patient's pulmonary artery blood pressure is a critical factor in diagnosing the heart failure patient and determining how best to manage the patient. Typically, blood pressure in the pulmonary artery has been determined by using a balloon-tipped pulmonary artery catheter having a pressure measurement function and sold under the trademark SWAN-GANZ, which is inserted and navigated through the right side of the patient's heart and the pulmonary valve into the pulmonary artery, a procedure that requires hospitalization. It has been estimated that there are about five million patients in the United States who suffer from heart failure with approximately one million hospital admissions per year to assess and treat the condition. It would be desirable to provide a means by which such data could be obtained before admitting the patient to the hospital as the patient may experience an improved quality of life and it might avoid the necessity for and cost of hospitalization.

It is among the general objects of the invention to provide a minimally invasive, improved means for controllably placing and supporting an implantable sensor within a body lumen in a position, location and sensor element orientation that facilitates the operation of the device, in which the means includes an anchor to which the sensor is mounted to achieve these objects. Also among the general objects of the invention is to provide an anchor-supported sensor and delivery device by which the anchor and sensor are retrievable from and repositionable within the body lumen.

SUMMARY OF THE INVENTION

In accordance with the invention, an implantable sensor or module is attached to an anchor of wire-like construction that is expandable from a low profile configuration, in which it can be delivered to the deployment site in the vessel, to an expanded configuration in which it is deployed in the vessel in engagement with the vessel wall. The self-expandable anchor may be formed from a highly resilient material, preferably one having superelastic properties, and includes at least one attachment strut by which the sensor is secured to and supported by the anchor. The sensor includes a housing with connector elements adapted to receive the attachment strut in a manner that fixes the position of the sensor relative to the axis of the attachment strut and prevents the sensor housing from rotating about the strut. The housing also or alternatively may contain components to perform therapeutic functions. The housing may have functionally active regions exposed along its outer surface.

In one embodiment of the invention the sensor housing may contain pressure-sensing components including an externally exposed sensing element that may also be called a functionally active region. The housing is mounted to the anchor such that, when the anchor is deployed, the sensing element of the sensor will face inwardly toward the center of the vessel lumen to be exposed fully to the pressure within the vessel. The anchor also may be configured to position the sensor housing adjacent the vessel wall to lessen the risk of turbulent flow through the vessel. The sensor housing also preferably contains a battery for powering the electronics associated with the device and communications electronics for wireless communication with other devices.

In another aspect of the invention, the implantable assembly is configured to be retrievable during and even after deployment in order to enable repositioning or removal of the assembly. The anchor of the assembly may be considered as being generally tubular, defined by a number of connected links or struts configured to be radially compressed to a low profile tubular configuration that is containable in the distal end of a delivery catheter. The anchor preferably includes a proximal region where it can be engaged by a delivery or retrieval device and drawn into the distal end of a tubular catheter or chamber while causing progressive compression of the anchor to its low diameter configuration. The sensor housing is attached to the anchor in a manner that allows for the radial compression of the anchor about the sensor housing such that both can be drawn into the delivery catheter. With the assembly so retrieved, the delivery catheter can be repositioned and the assembly redeployed in a different location or in a different orientation, or the device can be withdrawn from the patient in its entirety.

In another aspect of the invention the anchor includes a construction by which it can be engaged at a single point to facilitate retrieval into the distal end of a catheter or repositioning at another location in the vessel.

In yet a further aspect of the invention, the assembly is arranged to be short so that it be better able to pass through tortuous bends that may be encountered as the delivery device is navigated through the patient's vasculature. This is achieved by mounting the sensor within the anchor so that its ends do not protrude beyond the ends of the anchor.

In another aspect of the invention, a delivery device is provided for use with the anchor. The delivery device includes a rotatable helical coil contained in the lumen of an outer catheter shaft. The coil is adapted to engage or disengage the proximal portion of the anchor. The coil and outer sheath are moveable longitudinally relative to each other to enable the anchor to be drawn into the sheath or to expose the anchor and enable it to expand to a deployed configuration.

It should be understood that although the following description of the invention is principally in the context of placing and maintaining a sensor in the pulmonary artery to measure blood pressure, the invention is not limited to use in that context. The principles of the invention may be used to make implantable sensors assemblies adapted to measure and monitor any of a variety of physiological parameters in a variety of appropriate body locations.

DESCRIPTION OF THE DRAWINGS

The advantages, features, various aspects and objects of the invention will be appreciated more fully from the following description and accompanying drawings in which:

FIG. 2 is a diagrammatic plan view of an embodiment of an implantable sensor assembly including one embodiment of an anchor in an expanded configuration and incorporating principles of the invention;

FIG. 3 is a diagrammatic side view of the sensor assembly shown in FIG. 2;

FIG. 4 is an end view of the sensor assembly shown in FIG. 2, seen from the position 4-4 of FIG. 3;

DESCRIPTION OF THE ILLUSTRATIVE EMBODIMENTS

The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
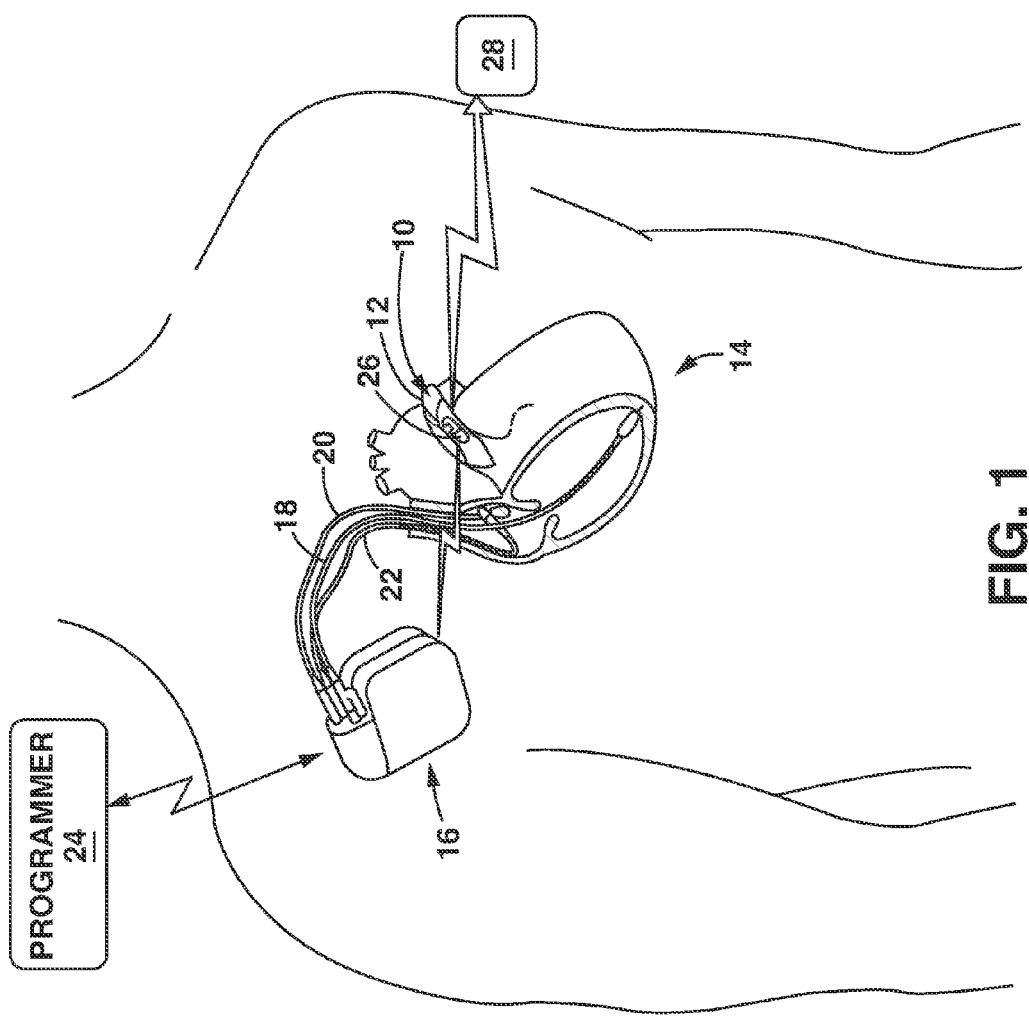
FIG. 1 is a diagrammatic illustration of a human patient depicting the locations of implantable medical devices including, for example, a pacemaker or defibrillator and a wireless sensor assembly placed in the pulmonary artery of the patient.
Figure 5:
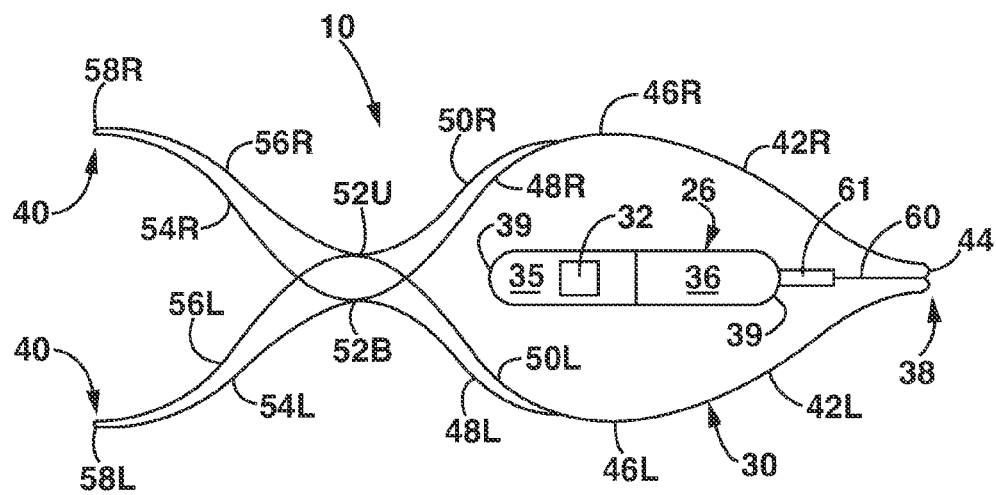
FIG. 5 is a slightly oblique isometric view of the sensor assembly of FIG. 2, seen from the angle indicated at 5-5 of FIG. 4.

FIG. 1 illustrates, diagrammatically, a patient with implanted medical devices including a sensor assembly 10 implanted, for example, in the patient's pulmonary artery 12 through which blood flows from the heart 14 to the lungs, and another device, such as a pacemaker, defibrillator or the like, indicated generally at 16. For purposes of this description, knowledge of cardiovascular anatomy is presumed and details are omitted except to the extent necessary or desirable to explain the context of the invention. The device 16 may have a number of leads 18, 20, 22 that are placed in electrical contact with selected portions of the cardiac anatomy in order to perform the functions of the device 16 as is well known to those skilled in the art. The device 16 also may have wireless capability to receive and transmit, by telemetry, signals relating to operation of the device. The device 16 may link wirelessly to an external device such as a programmer 24 or to another implanted device such as a sensor 26 of the sensor assembly 10. The sensor 26 also may communicate wirelessly with an external receiver 28 to provide in vivo data for selected physiological parameters to an external site to inform clinicians of the patient's status.

FIGS. 2-5 illustrate one embodiment of a sensor assembly 10 adapted for minimally invasive placement in a patient's blood vessel, the assembly being shown in its expanded configuration. The sensor assembly 10 includes a sensor 26 and an anchor 30 to which the sensor is attached. The anchor 30 and sensor 26 are arranged to enable the assembly to be collapsed to a low profile configuration to enable it to be carried by a delivery catheter and navigated to a deployment site where it can be released. Upon release, the anchor expands into sufficiently firm engagement with the wall of the blood vessel to maintain it in place. The sensor 26 is attached to the anchor 30 in a manner that when the anchor 30 is placed, the sensor 26, is located adjacent the wall of the vascular lumen to minimize adverse obstruction to blood flow through the lumen and to position the sensing element 32 of the sensor 26 to face towards the center of the blood vessel without obstruction from the body of the sensor or the vessel wall.

The sensor 26 includes a housing 34 preferably formed in two sections 35, 36, one of which (36) may contain a battery for powering the electronics and sensor components contained in the other section 35. The housing preferably is elongate and cylindrical in shape with rounded ends 39 and a cylindrical sidewall 41 extending between the ends 39. This shape is considered to present low resistance to blood flow. The sections are formed from a biocompatible material that can be hermetically sealed when the sections 36, 38 are joined. A number of such biocompatible materials may be employed, as will be understood by those familiar with the art, including metals and biocompatible plastics. For example, the sections 35, 36 may be formed from unalloyed titanium with an American Society for Testing and Materials (ASTM) grade 1 to grade 4 or an alloyed titanium (grade 5) that includes aluminum and vanadium. For embodiments in which the sections are metal, the metal should have sufficient malleability to facilitate secure attachment of the housing 34 to the anchor by crimping, as described in more detail below. The housing 34 as well as some portions of the anchor 30 may be encapsulated in a biologically inert dielectric barrier material such as a film of silicone or polyp-xylylene) polymer sold under the trademark PARYLENE. Those portions of the housing or anchor that are intended to serve as poles for intra-body wireless communication (e.g., to transmit or receive RF signals) may remain uncovered.

The anchor 30 is wire-like and, in this embodiment, includes a number of struts arranged to define a generally tubular shape that may be formed by laser cutting or etching a tubular blank or by other fabrication techniques well known in the art. The struts of the resulting anchor 30 typically have a substantially uniform radial thickness and may also have a substantially uniform width, which may be different from the strut thickness. Preferably, the anchor 30 is formed as a single, integral piece. For ease and convenience of explanation and orientation, the generally tubular anchor 30 may be considered as having a longitudinal axis 31 that defines the intersection of two orthogonally related planes, referred to as horizontal and vertical and indicated at X-X and Y-Y, respectively (FIGS. 2-4). Also for ease of explanation the anchor may be considered as having right and left sides on opposite sides of the vertical plane Y-Y as indicated by the arrows R and L in FIGS. 2 and 4. In the illustrative examples the anchors are symmetrical about the Y-Y plane.

As shown in FIGS. 2-5, the anchor 30 has a proximal end 38 and a distal end 40, the proximal end being adapted to be detachably connected to a delivery device as described in further detail below. The proximal region of the anchor 30 includes a pair of proximal struts 42L, 42R arranged to define a narrowed bight or crown at their proximal juncture 44. The juncture 44 defines anchor proximal end 38 and is offset radially from the axis 31 of the anchor, below the X-X plane, as shown. As seen in FIGS. 3 and 4 the struts 42L, 42R extend distally, sloping upwardly and diverging laterally from the juncture 44 and the Y-Y plane. The distal ends of the proximal struts 42L, 42R are attached, at second junctures 46L, 46R to two pairs of second struts 48L, 50L and 48R, 50R, respectively, that extend distally from their respective second junctures 46L, 46R. The distal ends of second strut pairs 48L, 48R converge toward each other and toward the Y-Y plane, as do the distal ends of the other second strut pair 50L, 50R. The distal ends of each pair of struts 48L, 48R and 50L, 50R are joined at a third junctures 52B, 52U, respectively, both of which preferably lie in the Y-Y plane below and above the X-X plane, respectively. Two pairs of third struts 54L, 54R and 56L, 56R extend distally and respectively from third junctures 52B, 52U, the struts in each pair being joined at distal junctures or crowns 58L, 58R that together define anchor distal end 40. The anchor 30 preferably is arranged so that in its fully expanded configuration its struts and junctures will lie along an imaginary surface that defines a circle in cross section such as, for example, a cylinder or cone. This may be seen from FIG. 4 in which the end view of a cylindrical device is depicted as a circle.

In the illustrated example of FIGS. 2-5 the sensor 26 may be attached to the anchor 30 by forming the anchor to include a linear, longitudinally extending attachment strut 60 to which the sensor housing may be secured. The strut 60 may be located at the proximal juncture 44, extending in a distal direction. A connector adapted to receive the strut may be mounted to or formed integrally with the housing, preferably on the housing section 34 that contains the battery, so that the other end of the housing will extend distally into the lumen defined by the anchor. The connector may take the form of a generally tubular connector socket 61 adapted to receive the free end of the attachment strut 60. Connector socket 61 may be located to extend from the proximal end of housing 34, as shown, or may take other forms, preferably secured to or integral with the battery section of the housing. For example, sensor housing 34 may include an elongate channel defined by deformable tabs adapted to receive the attachment strut transversely or may comprise a plastically deformable tube receptive to the attachment strut or other attachment elements. The connector socket 61 or other strut-receptive arrangement may be formed from the same material as that of the housing so as to be sufficiently malleable so that it can be plastically deformed about the attachment strut, as by a crimping operation to secure the two together. By way of further details of the foregoing connectors, see U.S. patent application Ser. No. 13/050,417 entitled Medical Device Fixation Attachment Mechanism and Ser. No. 13/090,869 entitled Implantable Medical Sensor and Fixation System, the disclosures of which are incorporated herein by reference.

Among the desirable aspects of the invention is that the sensor housing is attached to the anchor in a manner that does not require an increase in the length of the assembly 10. This is achieved by attaching the sensor housing so that it is disposed entirely between the ends of and within the lumen 59 defined by the anchor 30 (FIGS. 2-5). By avoiding an extended length of the sensor assembly 10 the associated delivery catheter may be better able to navigate tortuous vascular anatomy as it is advanced to the intended deployment site and the assembly may be better adapted to be placed in vessels in which the length of the device is a factor.

Figure 6:
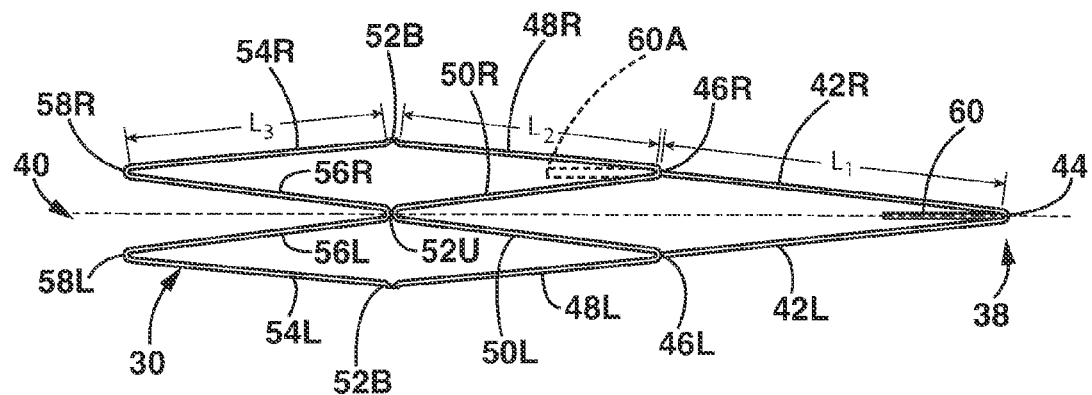
FIG. 6 is an illustration of the pattern, laid out in the flat, of the anchor of FIG. 5, as it may be laser cut or etched from tubular stock and before it is subjected to heat setting treatments.

FIG. 6 illustrates the pattern from which the anchor 30 is formed. For convenience, the pattern is shown in plan, as it would appear if the tubular member were slit longitudinally and spread on a flat surface. The anchor 30 may be made by laser-cutting the pattern from tubular stock of an appropriate material such as a superelastic nitinol alloy. After the pattern has been cut the tubular structure may be radially expanded to the selected design size and shape to which it will self-expand when unconstrained. While maintaining that expanded size and shape, as by maintaining it on a forming mandrel, the anchor is heat-treated to heat set the member in that selected expanded configuration. The expanded shape of the anchor 30 may be an imaginary cylindrical or frustoconical surface defined by the pattern of its struts and junctures although other configurations may be possible, depending on the application. Preferably the relaxed self-expanded diameter of the anchor should be of the order of about twenty percent greater than the effective lumen diameter at the target site of the vessel into which the sensor assembly is to be placed. The material of the anchor and its heat treatment may be varied in accordance with procedures well known to those skilled in the art to result in an anchor that is compressible to a low profile, flexible tubular configuration mountable onto or within a delivery catheter and that has a tendency to expand to its pre-set expanded shape and size when released and deployed at the intended site in the patient.

Figure 13:
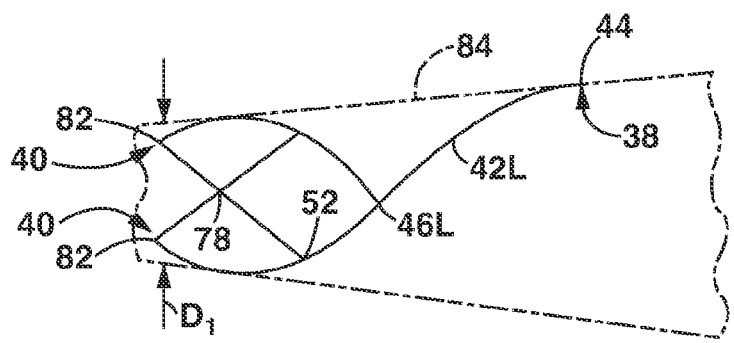
FIG. 13 is a diagrammatic side view of an anchor mounted on a tapered mandrel to be heat treated to assume that shape.
Figure 7:
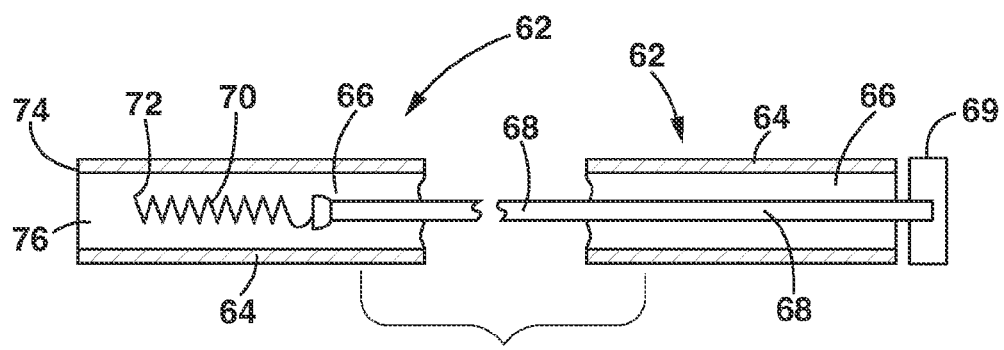
FIG. 7 is a fragmented diagrammatic illustration of a device that may be used to deliver and retrievably deploy the sensor assembly of FIGS. 2-4.

For application in the pulmonary artery tree we have determined that many patients for whom placement of such a device would be beneficial (e.g., patients suffering from heart failure) have a pulmonary artery tree with a region having a diameter of about ten millimeters at an accessible location, such as in the main, left or right pulmonary arteries. Thus, in an exemplary embodiment for use in the pulmonary artery tree, an unconstrained anchor 30 preferably is configured to have a distal taper such that the struts lie along an imaginary frustoconical surface. In FIG. 13, element 84 may considered as either the imaginary frustoconical surface or a tapered forming mandrel. By way of a preferred example, we have found that for use in the pulmonary artery, a cone taper angle of about twenty-two degrees, with an unconstrained distal diameter D1 of about twelve millimeters and a length, measured from proximal end 38 to distal end 40, of about forty five millimeters should enable placement of the device in a substantial majority of heart failure patients.

Figure 12:
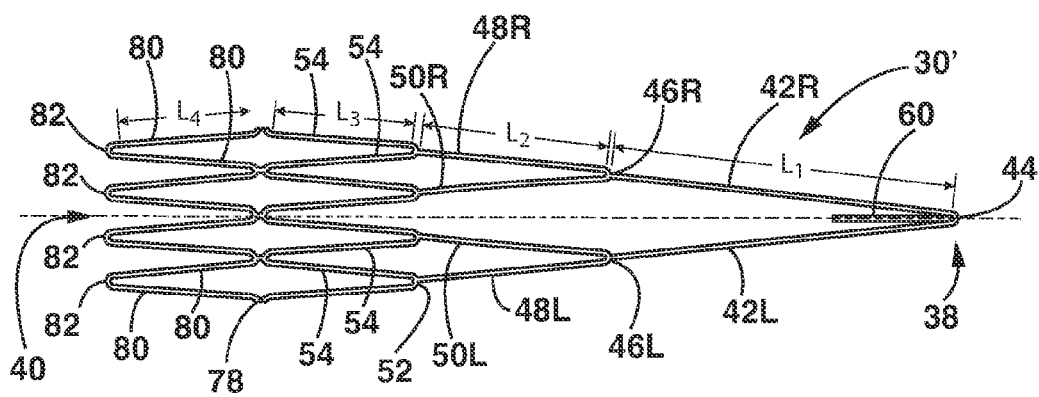
FIG. 12 is an illustration of the pattern, laid out in the flat, of a four-crown anchor, as it may be laser cut or etched from tubular stock and before it is subjected to heat setting treatments.

Additionally, the lengths of struts should be selected to be consistent with the geometry and number of groups of struts in the anchor. Different anchor embodiments may be referred to by the number of crowns that define the distal end 40. In the two-crown anchor of FIG. 6, which has fewer groups of struts, the struts may have the same lengths. In the example of FIG. 6 the lengths L1, L2, L3 may each be about 1.250 inches. In other embodiments having more groups of struts, such as the four-crown anchor described below and illustrated in FIGS. 12 and 13, the more proximal struts may be longer than the more distal struts. Thus, as indicated in FIG. 12 the proximal struts 42 having length L1 are longer than the next group of second struts 48, 50 having lengths L2. Similarly the second struts 48, 50 are still longer than third struts 54, 56 having lengths L3. Thus, with reference to FIG. 13, L1 is greater than L2, which, in turn is greater than L3. For example, in FIG. 13, L1, L2, L3 and L4 may be, respectively, may be about 0.800 inch, 0.350 inch, 0.300 inch and 0.280 inch. This results in an anchor that is more easily compressed to a low profile configuration at more proximal locations in that less force is required to effect the compression. It should be understood, however, that although we presently prefer the foregoing dimensions for pulmonary artery placement, variations may be made while incorporating the principles of the invention.

Figure 8:
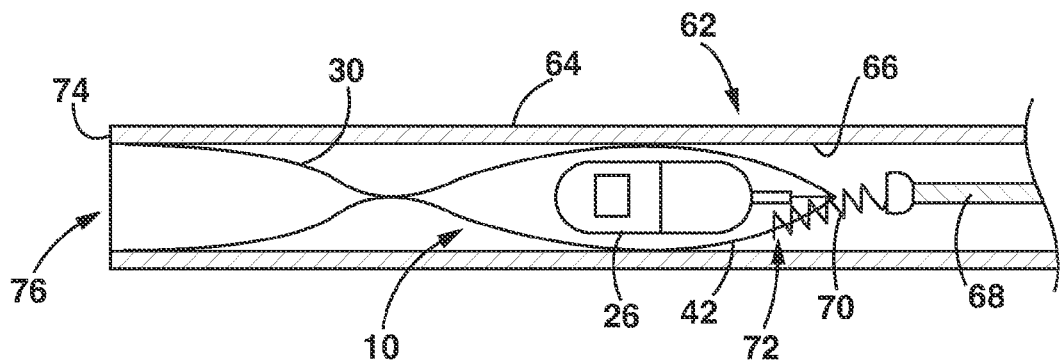
FIG. 8 is a diagrammatic illustration of the distal end of the delivery device of FIG. 7 with the sensor assembly contained in the device in its low profile delivery configuration.
Figure 9:
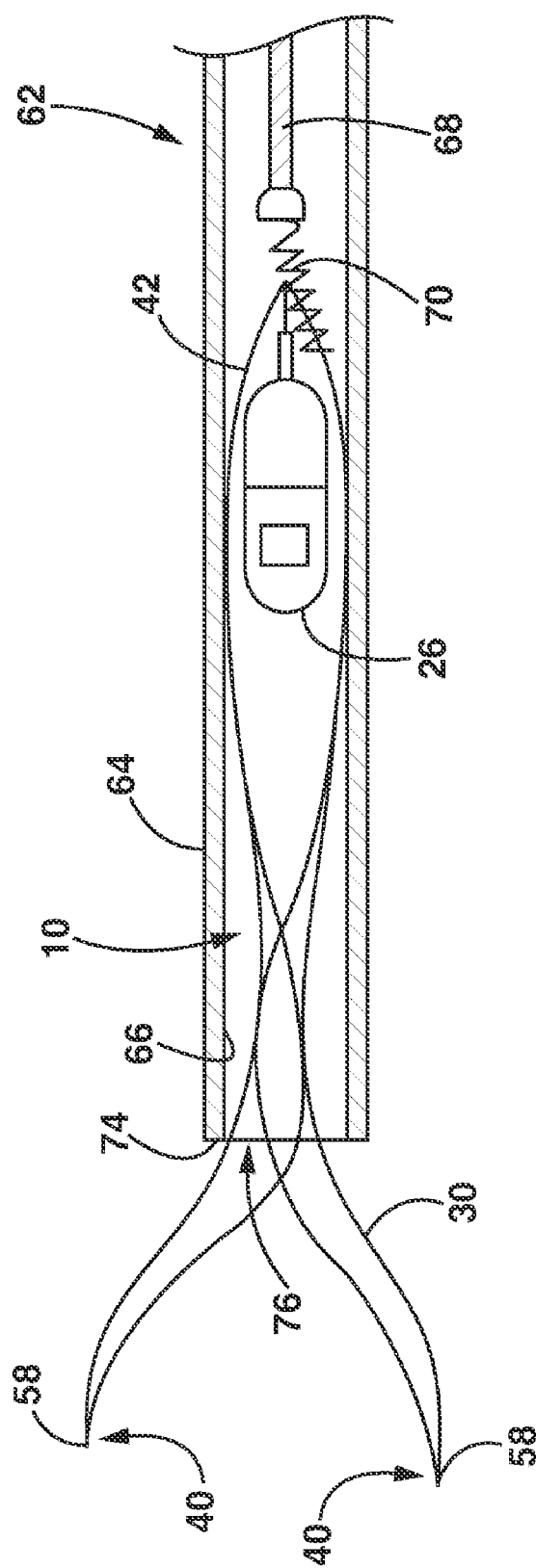
FIG. 9 is a diagrammatic illustration of the distal end of the delivery device with the catheter partly withdrawn and showing the sensor assembly in a partially deployed or partially retrieved state.
Figure 10:
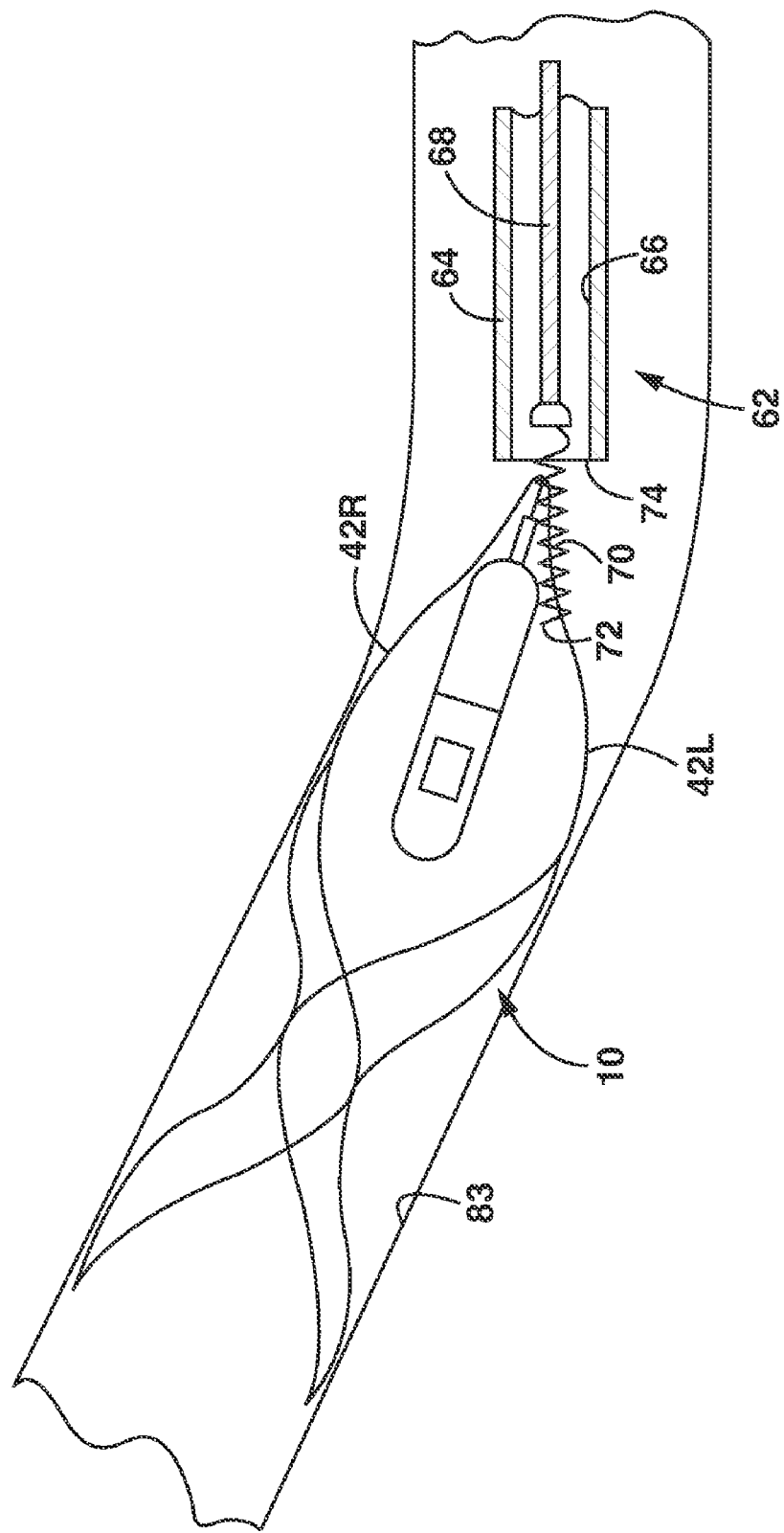
FIG. 10 is a diagrammatic illustration of the distal end of the delivery device of FIG. 7 with the catheter withdrawn and the sensor assembly in its expanded configuration in readiness to be released from the catheter or to be retrieved into the catheter.

FIGS. 7-10 illustrate, diagrammatically, a catheter delivery device 62 for a sensor assembly as described above, in progressive positions of deployment and retrieval. The delivery device 62 (FIG. 7) includes a catheter shaft 64 having a lumen 66 with a diameter, at least at its distal end, sufficient to receive and enclose the sensor assembly 10 in its compressed, low profile delivery configuration (FIG. 8). The delivery device 62 includes an internal rotatable shaft 68 that releasably attaches to the proximal end of the anchor 30, as by a helical coil 70 with a free distal tip 72 that can be wrapped about the proximal juncture 44 and/or one of the proximal struts 42L, 42R by rotation of the shaft 68. The shaft 68 and helical coil 70 may be rotated by a knob 69 or other control member attached to the proximal end of the rotatable shaft 68. The sensor assembly 10 is contained in the delivery catheter shaft 64 with the coil 70 in engagement with one of the proximal struts 42. The internal shaft 68 and the catheter shaft 64 are slidable longitudinally with respect to each other so that after the distal end of the delivery device 62 has been navigated to the intended deployment site, the catheter shaft 64 can be withdrawn proximally to remove its constraint about the anchor 30, enabling the anchor to self-expand within the lumen of the vessel (FIG. 10). Internal shaft 68 is sufficiently flexible, at least near the distal end, to permit proximal strut 42 to expand into apposition with the vessel wall. The clinician, at this juncture, can assess the placement of the sensor assembly and whether it is in its intended position and orientation. If so, the sensor assembly may be released from the delivery device by rotating the internal shaft 68 to unscrew the helical coil 70 from about the proximal strut 42 of the anchor. Should the clinician decide to reposition the sensor assembly before the coil 70 has been separated from the anchor, he may do so simply by advancing the catheter shaft 64 distally to engage and recapture the sensor assembly. If the assembly has been detached from the coil 70, the coil can be made to reengage the anchor by advancing the internal shaft 68 to lie adjacent one of the proximal struts 42 and then rotating the shaft 68 to cause the free end of the coil 70 to reengage the anchor.

The arrangement of struts and junctures results in a progressive drawing down of the anchor to its low profile configuration as the struts engage the mouth 74 of the distal opening 76 of the catheter. The configuration of the anchor 30 is such that as the mouth 74 of the distal opening 76 is advanced in a relatively distal direction it will engage progressively the proximal struts 42L, 42R to draw them together toward the axis 31 to a low profile configuration as the struts 42 are drawn into the lumen 66 of the catheter. As the proximal struts 42 are drawn together the second junctures 46L, 46R also are drawn together toward the axis 31 to also draw the third struts 48, 50 together to a low profile configuration (FIG. 9). The process continues with each set of struts drawing the next distal set inwardly to a low profile until all of the struts are drawn into the distal end of the lumen 66 (FIG. 8). Once recaptured, the device may be repositioned to redeploy the sensor assembly it or may be withdrawn from the patient.

When deploying the sensor assembly 10 the delivery catheter is positioned so that the sensor assembly will be located in a suitable selected deployment location where, when released, it will expand to engage the luminal surface 83 of the vessel wall sufficiently to hold the sensor assembly in place without applying excessive forces to that surface. Ideally the forces applied to the vessel wall should be just sufficient to hold the device in place without causing adverse trauma to the vessel. The forces to be applied are substantially less than, of the order of a fraction of, the applied forces associated with the placement of vascular stents in which the objective is to press against the vascular wall with sufficient force to dilate or provide scaffolding support for the vessel wall. By contrast, the present invention is intended merely to maintain the sensor assembly 10 in the vessel without migrating downstream while supporting the sensor 26 in its intended position and orientation. Thus, the deployed anchor should apply sufficient force to the vessel wall to maintain the position of the anchor but less than that for supporting the vessel wall.

When the sensor assembly 10 is deployed, for example, in a pulmonary artery, the catheter may be positioned to locate the distal end of the anchor at the selected deployment site, e.g., a location having a lumen with an effective diameter of about ten millimeters. When the clinician is satisfied with the placement, the catheter 64 may be withdrawn proximally while the sensor assembly is maintained in place by engagement with the coil 70. As the anchor expands, the sensing element 32 of the sensor 26 will be oriented to face the center of the lumen to be exposed fully and without obstruction to blood flow in the lumen. The sensor assembly is supported so that it will lie in close proximity to and preferably against the wall of the lumen to present a lessened risk of turbulent blood flow.

Figure 11:
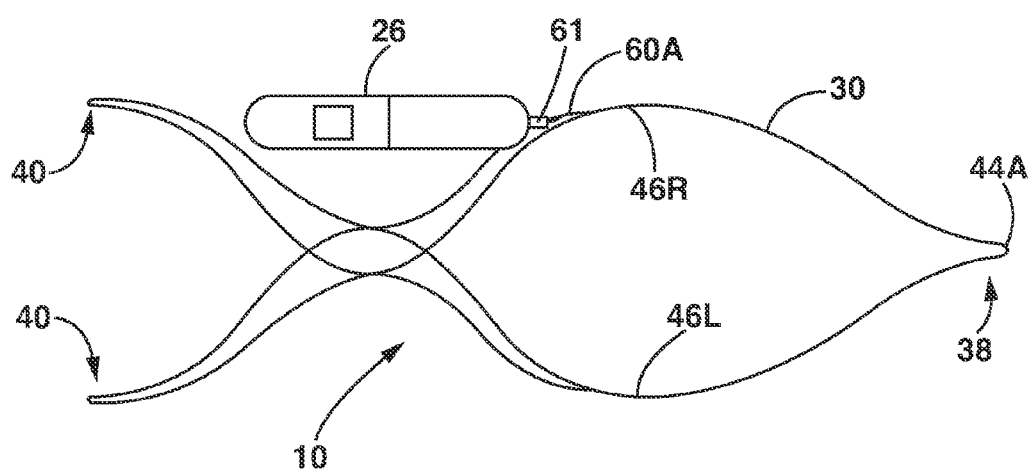
FIG. 11 is an illustration of a sensor assembly having an anchor configured similarly to that of FIGS. 2-5 with the sensor being attached to the anchor at a more distal location.

FIG. 11 shows a sensor assembly having a similar anchor as described above in connection with FIGS. 2-5 except that the sensor 26 is mounted to a more distal location on the anchor. In this embodiment the anchor includes an attachment strut 60A that extends distally from one of the second junctures 46. FIG. 6 also shows (in phantom) alternative attachment strut 60A. In this embodiment, anchor proximal end 38 may be defined by a simple crown or bight 44A. The sensor housing may be secured to the attachment strut in the same manner as described in connection with the embodiment of FIGS. 2-5.

FIG. 12 illustrates a pattern, in the flat, for another embodiment of an anchor 30' in which its distal end 40 may be considered as being defined by four crowns or distal junctures 82. Here, the anchor includes a proximal end 38 defined by juncture 44 and a pair of distally extending proximal struts 42L, 42R, each of which terminates in a second juncture 46L, 46R, respectively. Two pairs of second struts 48L, 50L and 48R, 50R extend distally from each of the second junctures 46L, 46R, respectively, each of second struts 48L, 50L and 48R, 50R terminating in a respective third juncture 52. A pair of third struts 54 extends distally from each of the third junctures 52 resulting in an arrangement of eight third struts 54. The distal ends of the third struts 54 are joined in pairs to form four fourth junctures 78. Should it be desired to increase the length of the four-crown anchor device 30' an additional set of eight (fourth) struts 80 may be provided to extend distally in pairs from the fourth junctures 78, the distal ends of those fourth struts being joined together in pairs at four distal junctures 82. Attachment strut 60 is shown extending distally from the first juncture 44. As described above in connection with the pattern of FIG. 6 the struts closer to the proximal end of the anchor preferably are longer than those more distally located. Thus, in FIG. 12 L1 is greater than L2, L2 is greater than L3 and L3 may be greater than L4. In some cases, however it may be preferred to make the most distal group of struts about the same length as the immediately proximal group if making the most distal struts would result in too great a force requirement to compress the anchor to the low profile configuration.

FIG. 13 illustrates, diagrammatically, a four-crown anchor mounted on a tapered mandrel, shown in phantom at 84 to form a device for use in the pulmonary arteries. The anchor, after having been formed from tubular stock is expanded to fit on the mandrel and is subjected to a heat treatment protocol to fix the elastic memory of the anchor in the selected size and taper. In the resulting anchor all of the struts and junctures will tend to lie on an imaginary frustoconical surface corresponding to that of the tapered mandrel.

Figure 14:
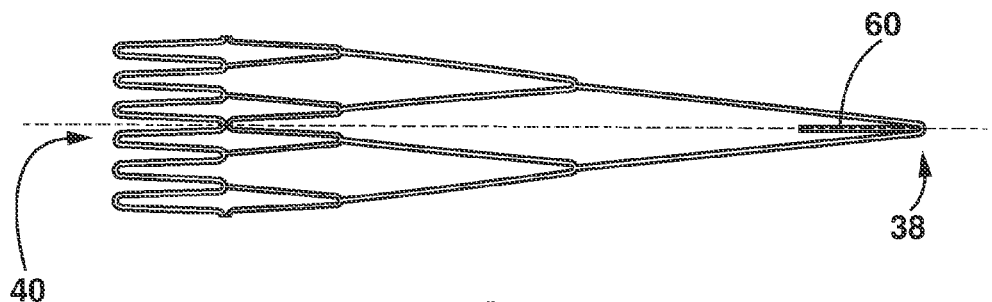
FIG. 14 is an illustration of the pattern, laid out in the flat, of a six-crown anchor as it may be laser cut or etched from tubular stock and before it is subjected to heat setting treatments.
Figure 15:
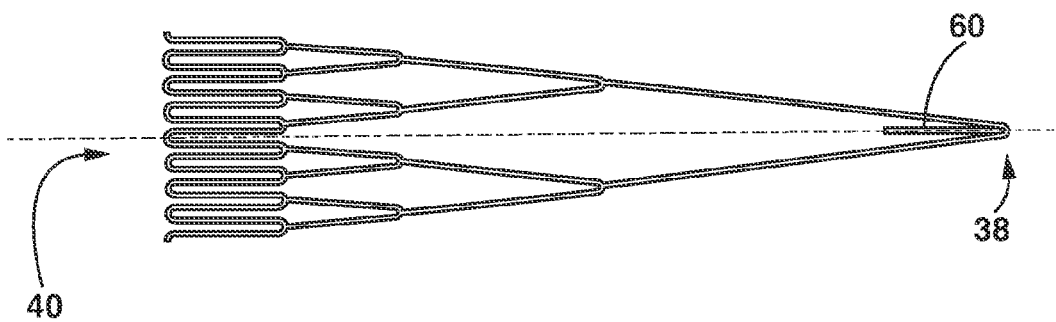
FIG. 15 is an illustration of the pattern, laid out in the flat, of an eight-crown anchor as it may be laser cut or etched from tubular stock and before it is subjected to heat setting treatments.

It should be noted that an anchor incorporating the principles of the invention may be provided with a greater number of distal crowns if desired. FIGS. 14 and 15 illustrate patterns, in flat for forming anchors with six or eight crowns, respectively.

It should be understood that the foregoing examples of embodiments of the invention are illustrative only and that other embodiments, modifications and equivalents may be apparent to those skilled in the art that nevertheless are within and embody the principles of the invention.

We claim:

1. A method of implanting a medical device in a selected region of a lumen of a human patient, the selected region having an effective diameter comprising:
   receiving a medical device that includes a diagnostic or therapeutic module and an anchor, the anchor having proximal and distal ends and being self-expandable from a low profile, in which it can be delivered to the selected region, to an expanded configuration having an effective diameter greater than the effective diameter of the selected region of the lumen to enable the anchor to expand in the lumen into pressing engagement with the wall of the lumen, the effective diameter and structure of the anchor being arranged to enable the anchor to bear against the lumen wall with force sufficient to maintain the anchor in place but insufficient to provide structural support for the lumen, the anchor further having a plurality of struts interconnected at junctures to define a tubular configuration with proximal and distal ends, the proximal end of the anchor being defined by a pair of proximal struts connected at a single proximal juncture and an attachment strut extending in a distal direction from one of the junctures, the diagnostic or therapeutic module having a connector receptive to the attachment strut, the connector being securely connected to the attachment strut, the attachment strut and connector being arranged to orient the diagnostic or therapeutic module within and between the ends of the anchor;
   navigating the medical device to the selected region of the lumen while maintaining it in its low profile configuration by confining the anchor within a distal chamber of a delivery catheter and engaging the proximal end of the anchor with a retention member of the delivery catheter;
   removing the confining chamber of the catheter from about the anchor while maintaining the retention member in engagement with the proximal end of the anchor, thereby enabling the anchor to expand against the selected region of the lumen;
   confirming the position of the deployed medical device within the patient's lumen; and
   after the desired position is confirmed, releasing the retention member from the proximal end of the anchor.

2. The method of claim 1 wherein the effective diameter of the anchor in its expanded state is about twenty percent greater than the effective diameter of the selected region of the lumen.

3. The method as defined in claim 1 further comprising:
   before releasing the medical device recapturing the anchor within the confining chamber while causing the anchor to return to its low profile configuration within the chamber;
   repositioning the delivery catheter to another selected region of the lumen;
   redeploying the medical device and confirming the position of the deployed medical device within the patient's lumen; and
   after the desired position is confirmed, releasing the retention member from the proximal end of the anchor.

4. The method as defined in claim 1 wherein the desired position is not confirmed and further comprising:
   recapturing the anchor within the confining chamber while causing the anchor to return to its low profile configuration within the chamber;
   and removing the catheter and medical device from the patient.

5. The method as defined in claim 1 wherein the proximal end of the anchor comprises a pair of proximal struts joined at a single crown at their proximal ends.

6. The method as defined in claim 5 wherein the retention member engages the proximal end of the anchor at a proximal strut or the single crown.

7. The method as defined in claim 1 wherein when the medical device is in its expanded position the module is disposed adjacent the wall of the lumen.

8. The method as defined in claim 7 wherein the module has a functionally active region along its outer surface and wherein the functionally active region faces inwardly into the lumen when the device is deployed.

9. The method as defined in claim 1 further comprising:
the lumen comprising a pulmonary artery;
the struts and junctures being arranged, when the anchor is in its expanded configuration, to lie along and define an imaginary conical surface, the distal end of the anchor defining a diameter of about twelve millimeters, the conical surface defining a cone angle of about twenty two degrees;
the diagnostic or therapeutic module being disposed adjacent the vessel wall with a sensing element disposed along a module outer surface facing the lumen of the vessel;
locating a region of the pulmonary artery having an effective diameter of about ten millimeters;
deploying the distal portion of the anchor in that region of the pulmonary artery.

10. The method as defined in claim 1 wherein the retention member comprises a helical coil rotatable within the delivery catheter, the coil having a distal terminus defined by a free end;
the coil being in detachable engagement with the proximal end of the anchor;
and wherein the step of releasing the anchor comprises rotating the coil in a direction to separate the coil from the free end of the anchor.

11. The method as defined in claim 10 further comprising:
before releasing the medical device recapturing the anchor by rotating the coil in a reverse direction to reengage the free distal end of the coil with the proximal end of the anchor and while reengaged, advancing the confining chamber over the anchor to cause the anchor to return to its low profile configuration within the chamber;
repositioning the delivery catheter to another selected region of the lumen;
redeploying the medical device and confirming the position of the deployed medical device within the patient's lumen; and
after the desired position is confirmed, releasing the retention member from the proximal end of the anchor.

12. The method as defined in claim 10 wherein the desired position is not confirmed and further comprising:
recapturing the anchor within the confining chamber while causing the anchor to return to its low profile configuration within the chamber; and
removing the catheter and medical device from the patient.

* * * * *